US007608037B2

(12) United States Patent
Levy

(10) Patent No.: US 7,608,037 B2
(45) Date of Patent: Oct. 27, 2009

(54) REMOTELY LOCATED PLEASURE DEVICES

(75) Inventor: David H. Levy, Cambridge, MA (US)

(73) Assignee: TH, Inc., Berkeley, CA (US)

( * ) Notice: Subject to any disclaimer, the term of this patent is extended or adjusted under 35 U.S.C. 154(b) by 256 days.

(21) Appl. No.: 11/531,224

(22) Filed: Sep. 12, 2006

(65) Prior Publication Data

US 2007/0049792 A1 Mar. 1, 2007

Related U.S. Application Data

(63) Continuation-in-part of application No. 10/260,330, filed on Sep. 30, 2002, now Pat. No. 7,104,950, which is a continuation-in-part of application No. 09/609,526, filed on Jul. 3, 2000, now abandoned.

(60) Provisional application No. 60/141,884, filed on Jul. 2, 1999.

(51) Int. Cl.
*A61F 5/00* (2006.01)

(52) U.S. Cl. ........................................................ 600/38

(58) Field of Classification Search ................. 600/300, 600/38–41; 128/897, 898, DIG. 25
See application file for complete search history.

(56) References Cited

U.S. PATENT DOCUMENTS

| | | | |
|---|---|---|---|
| 494,410 | A | 3/1893 | Carpenter |
| 734,498 | A | 7/1903 | Bachler |
| 1,413,789 | A | 4/1922 | Schaff |
| 1,729,296 | A | 9/1929 | Sarason |
| 3,259,132 | A | 7/1966 | Katter |
| 3,495,589 | A | 2/1970 | Clement |
| 3,598,106 | A | 8/1971 | Buning |
| 3,752,150 | A | 8/1973 | Harris |
| 3,991,751 | A | 11/1976 | O'Rourke |
| 3,996,930 | A | 12/1976 | Sekulich |
| 4,050,449 | A | 9/1977 | Castellana et al. |
| 4,167,938 | A | 9/1979 | Remih |
| 4,776,347 | A | 10/1988 | Matthews |
| 5,072,720 | A | 12/1991 | Francis et al. |
| 5,131,906 | A | 7/1992 | Chen |
| 5,256,123 | A | 10/1993 | Reinbolt |
| 5,573,499 | A | 11/1996 | McAllister |
| 5,674,238 | A | 10/1997 | Sample et al. |
| 5,690,603 | A | 11/1997 | Kain |
| 5,690,605 | A | 11/1997 | Hamlin et al. |
| 5,704,894 | A | 1/1998 | Boutos |
| 5,724,994 | A | 3/1998 | Simon et al. |
| 5,885,205 | A | 3/1999 | Kassman |
| 6,165,108 | A | 12/2000 | Ralston |
| 6,179,795 | B1 | 1/2001 | Garza |
| 6,368,268 | B1 * | 4/2002 | Sandvick et al. .............. 600/38 |

FOREIGN PATENT DOCUMENTS

| | | | |
|---|---|---|---|
| WO | WO 88/06077 | * | 8/1988 |

* cited by examiner

*Primary Examiner*—Samuel G Gilbert
(74) *Attorney, Agent, or Firm*—Fish & Richardson P.C.

(57) ABSTRACT

A sexual preference transfer function that combines the masturbatory action of a first person with the expressed or non-expressed sexual preferences of a second person. A sexual preference transfer function is utilized to improve the control or influence of a sexual pleasure device in contact with a second person based on autonomic and/or manually collected data.

22 Claims, 3 Drawing Sheets

Transfer Function Correlations

| Source | Input Data | | Output Response |
|---|---|---|---|
| First Person | Amplitude (Duration) | | |
| | Frequency (Duration) | | |
| | Force (Duration) | | |
| | Direction (Duration) | | |
| | Auxiliary motion (Duration) V | | |
| | Vocalizations | | |
| Second Person | Amplitude (Duration) | Transfer Function | Amplitude |
| | Frequency (Duration) | | Frequency |
| | Force (Duration) | | Force |
| | Direction (Duration) | | Direction |
| | Auxiliary motion (Duration) | | Auxiliary motion |
| | Physiological Data (Duration) | | Randomization |
| Stored Control Data | Stored Control Data | | |

FIG. 5

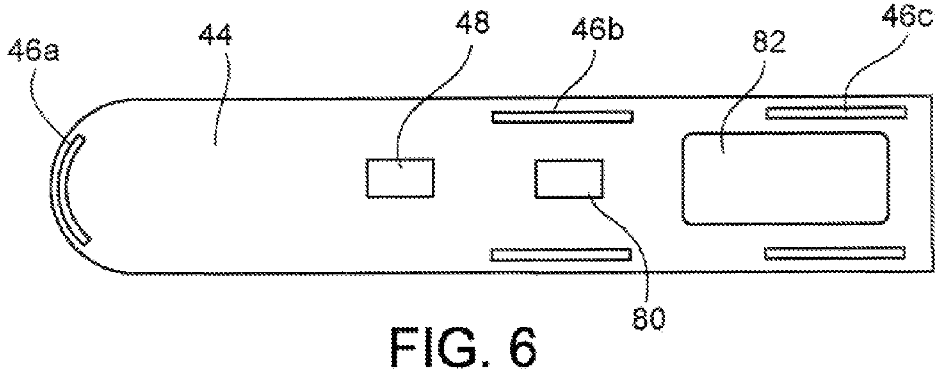

FIG. 6

REMOTELY LOCATED PLEASURE DEVICES

CROSS-REFERENCE TO RELATED APPLICATIONS

This application is a continuation-in-part of U.S. application Ser. No. 10/260,330, filed Sep. 30, 2002, now U.S. Pat. No. 7,104,950, which is a continuation-in-part of U.S. application Ser. No. 09/609,526, filed Jul. 3, 2000, now abandoned, which claims the benefit of the filing date of provisional application 60/141,884, filed Jul. 2, 1999, now expired. The complete disclosures of these prior applications are incorporated herein by reference in their entirety.

TECHNICAL FIELD

This disclosure relates to providing optimized physical pleasure between two persons at remote locations.

BACKGROUND OF THE INVENTION

What is desirable is a system that optimizes physical pleasure between remotely located persons. It is also desirable for the system to provide a level of customization to the needs of recipient partners that could not be provided with direct physical contact. It is further desirable for a system to provides sexual sharing in which the “output” (stimulus to a recipient partner) is largely transparent to both parties (i.e. one party should not be focused on the control of a device for the other partner). It is also desirable to provide a system that allows the motions of self-pleasure of one person to influence the self-pleasure of another. It is further desirable to provide a system that allows sexual partners with differing sexual patterns to each have their disparate needs addressed simultaneously. U.S. Pat. No. 6,585,668 to Nissim describes a massage robot, however it is not under the control of a person, nor is the origin of the control located remotely to the recipient.

SUMMARY OF THE INVENTION

The limitations described above are superseded, and objects and advantages achieved by the following:

In massage it is not uncommon for the masseuse to press too hard or not enough, either generally or to localized areas. Sometimes the person is incapable of pressing with the high level of force desired by the recipient, or would grow weary by doing so. With remote massage (a message mechanism such as a chair or arm that is under the direct control of a remotely located masseuse) the recipient may amplify, or diminish, the actions of masseuse, who may be touching a remotely located generic model of the human body. The recipient may add high frequency, low amplitude stimulus (vibration) to the large scale motions of the masseuse, or low frequency higher amplitude motion that will provide an oscillatory pressure superimposed on the masseuse’s intended motions. The transfer function that drives the output is comprised of the motions of a first person as modified by input from the recipient. The result is a massage that has the capability of providing sensations that are not possible with a direct human-to-human massage. The sensory customization provided by the transfer function may be specified by region of the body to add, detract or modify the sensations in a predetermined fashion, or spontaneously.

In one example, motions of self-pleasure of a first person are used to modulate an electronically controlled pleasure device to provide sexual pleasure to a second (recipient) person, e.g., through a data or audio communication means. The recipient may be passive, or self-pleasuring as well. In the latter case the motions of the first person are superimposed upon the motions of the recipient. Each partner (potentially more than two) may have their motions sensed and subsequently used as the control signal to recipients. While partners may be in the same room, the larger advantages of the system are provided by remotely located partners. Pleasure devices which may be electronically controlled in this manner can include, e.g., a vibratory device, a thrusting device, a device with rotating beads, a Sybian, or any other such pleasure device that contains electronics.

According to one aspect, a method for remote delivery of physical sensations includes measuring a physiological motion of a first person situated at a first location and reducing the measured motion of the first person to a set of motion data. The method also includes transmitting the motion data to a remotely located receiving unit, utilizing the motion data to provide a physical stimulus, and administering the physical stimulus to a second person situated at a second location remote from the first location.

The physiological motion can include a motion of a hand, e.g., a motion of sexual self-gratification by the first person. Various means may be used to collect the motion data from the first person. For example, in one embodiment, a cuff, with a plurality of sensors is used to measure muscular contraction at various locations of the forearm, using force, galvanic or other methods as known in the art. In another example, a camera is used to collect raw data of hand motion. Still, in another embodiment, sensors arm located inside a pleasure device, such as pressure sensors or accelerometers inside a dildo. Regardless of the specific method used to collect motion data, this data is provided to a to microprocessor where it is correlated with specific classes of motions that need only be known internal to the system. These classes of motion correlate with the variations associated with self-pleasuring such as displacement, velocity, acceleration and location of the hand or pleasure device, as well as degree of force being applied. Motion data can be measured with respect to individual fingers of the hand, as each portion of the wrist, both contractile and extensile may be measured. Additional data can also be collected by voice recognition, verbal stimulus that may be used to modify the physical sensations provided to each receptive partner. Voice data may also be utilized, either for it’s magnitude, or specific words may be detected with voice recognition. This input data (i.e., the set of control data), or a modified version of it, is transmitted, e.g., by an audio or data channel such as telephone or computer data line, to electronics (i.e., output correlation electronics) that control an electronically controlled device (i.e., pleasure device) attached to and/or operated by a second person such that motions from the first person contemporaneously affect operation of the recipient device.

In some cases, utilizing the motion data to provide a physical stimulus includes delivering an output signal, corresponding to and/or correlated to control data, to a pleasure device. In some cases, the physical stimulus is superimposed on a physiologic motion of the second person. In some embodiments, the method can also include controlling the pleasure device to provide motions that correlate to a predefined set of control parameters based at least in part on the output signal. In some implementations the predefined set of control parameters correspond to sexual preferences of the second person. In some cases, the predetermined set of control parameter include one or more of a frequency of vibration, an amplitude of vibration, a change in three-dimensional shape of the device, a change in temperature of the device, a thrusting motion, application of pressure, and/or a change in direction or magnitude of an applied force.

In some embodiments, a set of control parameters are received from the second person (i.e., recipient) and the output signal is adjusted based on the set of control parameters, thereby customizing the physical stimulus to the second person. In one embodiment, a transfer function correlates the classes of motions originating from a first person (i.e., the set of control data) with the set of control parameters (e.g., potentially different classes, magnitudes, or phase of output response provided to the recipient device) such that the recipient receives output motion (or non-motion) pleasure stimuli customized to the recipient, and the device of the recipient. The objective is to correlate the motions of the first person with pleasuring patterns specific to the receptive person. For example, in some cases, the set of control parameters corresponds to a natural sexual pattern specific to the second person. Thus, the instant invention allows two individuals with disparate pleasuring patterns to achieve sexual parity to a higher degree than they could without it, whether or not they are co-located. As one example, a first person who initiates high amplitude, low frequency motions early in the process and then low amplitude, high frequency motion near the end could (using the instant invention) cause the opposite effect in the pleasure means of the second person (who prefers low amplitude, high frequency motions early in the process and high amplitude, low frequency motion at the end) by selection of the appropriate transfer function. This invention therefore provides means for a first person to self-pleasure themselves in such a way as to simultaneously create a pleasure stimulus in a remotely located person such that the remotely located person is pleasured in a way that is also optimized, yet transparent to the first person. This can include the second person self-pleasuring themselves with a device that includes mechanical actuation controlled by the motions of self-pleasure of the first person such that the stimulation received by the second person is a combined effort of their own actions and those the remotely located first person. Furthermore, in this class of device the system can operate in both directions simultaneously, so that each partner experiences their own self-pleasure with additional independent motions superimposed as a consequence of the output from the self-pleasure of the partner. A simple example would be two handheld vibratory devices. The large-scale motion of the device would be self-controlled. The amplitude and frequency of vibration (for both partners) would be passively controlled by the large-scale motions of the remotely located partner.

In some implementations, the transfer function between partners is intentionally altered to optimize the experience for the second (receptive) person. This resolves differences in the eventuality that the second person has a different natural pleasure rhythm than the first. This allows the recipient to be optimally pleasured "transparent" to the first person, regardless of the natural manner of self-pleasure of the first person The selection/modification of the transfer function is affected by the system in a manner that is user-friendly to users, so they are only aware of the end-result. For example, in some embodiments, the transfer function is generated by the second person while the invention is in a manual or "learn" mode. At any time during a "learning" process, the second person may modify the output and thereby the transfer function. The system learns what the second (receptive) partner prefers as a function of what the available inputs and available stored data, including the time the second person chooses to spend with each transfer function setting. The settings may also be created by a questionnaire. The system therefore builds a customized mapping of input to optimal output as a function of the input class, the phase of the process (as a function of time or measured physiologic response of one or both partners) and the output previously selected by the receptive person under similar sets of conditions in the past.

Some embodiments include an integration of autonomic physiologic data and or self-evaluated physiologic information into the transfer function and utilizing this data to vary the output(s) as a function of the physiologic state of one or both partners. For example, in some cases, a set of control parameters received from the second person includes a measured physiologic state of the second person. This measured physiologic state can be reduced to a corresponding set of data that can be correlated with the set of control data (i.e., the data corresponding to the measured motion of the first person). This physiologic state/data may be measured utilizing various means known in the art, e.g., with a preference to the means described herein. Using these devices and methods, a given motion by a first person may result in a different output response in the device used by a second person, as a function of time, learned history, and/or physiologic response of the second person. Randomized motions, or randomized motions superimposed upon intended motions may also be included in the sequence. This variation is provided by existence of a dynamically modifiable transfer function that correlates the information described and modifies the output accordingly.

According to another aspect, a remotely operable personal massaging system includes one or more sensors configured to measure a physiological motion of a first person and data acquisition electronics configured to receive an input signal representing the measured physiological motion from the sensors. The data acquisition electronics are configured to convert the input signal to a corresponding set of motion data. The system also includes data transmission electronics in communication with the data acquisition electronics. The data transmission electronics are configured to transmit an output signal (e.g., a series of information packets) representing the set of motion data to a remote location. A primary pleasure device, operable to deliver a physical stimulus to a second person, is provided at the remote location. The system also includes an output correlation unit disposed at the remote location and configured to receive the output signal from the data transmission electronics. The output correlation unit includes signal conditioning electronics configured to drive the pleasure device according to a predetermined actuation sequence correlating to the output signal.

In some examples, the sensors can be disposed in a secondary pleasure device operable by the first person. The sensors can be configured to measure one or more of: an amplitude of vibration, a mode of oscillation, a magnitude of force, and a direction of force. For example, the sensors can be pressure sensors, strain gauges, galvanic sensors, and/or accelerometers.

In some embodiments, the system includes an input module disposed at the remote location. The input module is configured to receive a set of control parameters from the second person and deliver a set of output data, corresponding to the set of control parameters, to the output correlation unit. In these cases, the output correlation unit is configured to adjust the predetermined actuation sequence in response to receiving the set of output data from the input module. The set of control parameters can, for example, correspond to a natural sexual pattern of the second person.

In some implementations, the set of control parameters comprises physiologic data (e.g., blood pressure, blood oximetry, and skin conductivity) unique to the second person. The input module can include one or more secondary sensors configured to measure the physiologic data.

Generally, motions of a first person can be correlated to a physical stimulus sensed by a second person, situated in location remote from the first person, through a transfer function. In one aspect, a transfer function is stored on a computer readable medium. The transfer function includes a first input module, configured to receive an input data packet corresponding to a set of measured hand motions originating from a first person, and a second input module, configured to receive a set of control parameters from a second person, situated in a location remote from the first person. The transfer function also includes a transfer algorithm adapted to correlate the input data packet with the set of control parameters and to provide a corresponding output signal, thereby to control an operation of a pleasure device for delivering a physical stimulation (e.g., a sexual stimulation) to the second person. For example, in some cases, the transfer function can be implemented to correlate a masturbatory motion of the first person to a sexual stimulation sensed by the second person.

According to yet another aspect, a physiological-motion measuring device includes a cuff element configured to be worn about a forearm of a user. One or more muscular sensors (e.g., piezoelectric sensors, strain gages, or galvanic sensors) are carried by or on the cuff element. The muscular sensors are configured to measure muscular contraction at various locations of the user's forearm. The muscular sensors are configured to provide an output corresponding to an overall physiological motion displacement of the user.

In some implementations, the device also includes one or more accelerometers each carried by or in a corresponding band to be worn about a finger of the user, and configured to measure a physiological motion of the corresponding finger, preferably, the accelerometer carrying band does not extend to the palm side of the user's finger during use. In some cases, the device includes one or more secondary muscle sensors each carrier by or in a corresponding band to be worn about a finger of the user, and configured to measure muscular contraction of the corresponding finger. In some embodiments, the device includes one or more accelerometers carried by or on the cuff element and configured to cooperate with the muscle sensors and primary accelerometers to provide the an overall physiological motion displacement of the user. The device can also include one or more secondary sensors each attached to a corresponding finger of the user with an adhesive, wherein the secondary sensors are configured to measure a physiological motion of a corresponding finger, and to cooperate with the muscular sensors to provide an overall physiological motion displacement of the user.

According to another aspect, a physiological-motion measuring device includes a cuff element configured to be worn about a forearm of a user and a primary accelerometer carried by or on the cuff element. The primary accelerometer is configured to measure physiological motion of the user's forearm, and to provide an output corresponding to the measured physiological motion.

Implementations of this aspect can include one or more of the following additional features. The device can include one or more muscular sensors carried by or on the cuff element, wherein the muscular sensors are configured to measure muscular contraction at various locations of the user's forearm, and to cooperate with the primary accelerometer to provide an overall physiological motion displacement of the user. The device can include one or more secondary sensors (e.g., accelerometers and/or muscular sensors, e.g., piezoelectric sensors, strain gages, or galvanic sensors) each carried by or in a corresponding band to be worn about a finger of the user, wherein the secondary sensors are configured to measure a physiological motion of a corresponding finger, and to cooperate with the primary accelerometer to provide an overall physiological motion displacement of the user. The device can include one or more secondary sensors each attached to a corresponding finger of the user with an adhesive, wherein the secondary sensors are configured to measure a physiological motion of a corresponding finger, and to cooperate with the primary accelerometer to provide an overall physiological motion displacement of the user.

In yet another aspect, a method of sharing sexual pleasure between remotely situated individuals includes measuring motions of self-pleasure of a first person using a first pleasure device and transmitting a data signal corresponding to the measured motions to a second pleasure device, disposed in a location remote from the first pleasure device. The method also includes, correlating the data signal with an output signal according to a transfer function and driving the second pleasure device with the output signal, thereby to provide a physical stimulus of a sexual nature to a second person using the second pleasure device.

Implementations of this aspect can include one or more of the following additional features. The method can include superimposing the physical stimulus of the second pleasure device with a physiological motion of the second person. In some cases, the method also includes measuring motions of self-pleasure of the second person using the second pleasure device; transmitting a second data signal corresponding to the measured motions of self-pleasure of the second person to the first pleasure device; correlating the second data signal with a second output signal according to a second transfer function; and driving the first pleasure device with the second output signal to provide a physical stimulus of a sexual nature to the first person based on the measured motions of self-pleasure of the second person. The method can also include, receiving a set of control parameters from the second person, wherein the control parameters are used to influence the physical stimulus of the second device. In some cases, the second person has dynamic (i.e., contemporaneous with the output signal) control over the control parameters of the second device, but has no direct physical control (i.e., hand contact) of the second device. The system dynamics, electronics and network technology needed to effect the invention described herein are well known in the art.

Other features and advantages of the invention will be apparent from the following detailed description, and from the claims.

BRIEF DESCRIPTION OF DRAWINGS

FIG. 5 shows a table with examples of transfer function correlations.

FIG. 6 shows a pleasure device augmented with sensors to provide input to the instant invention.

DETAILED DESCRIPTION OF DRAWINGS

Figure 1:
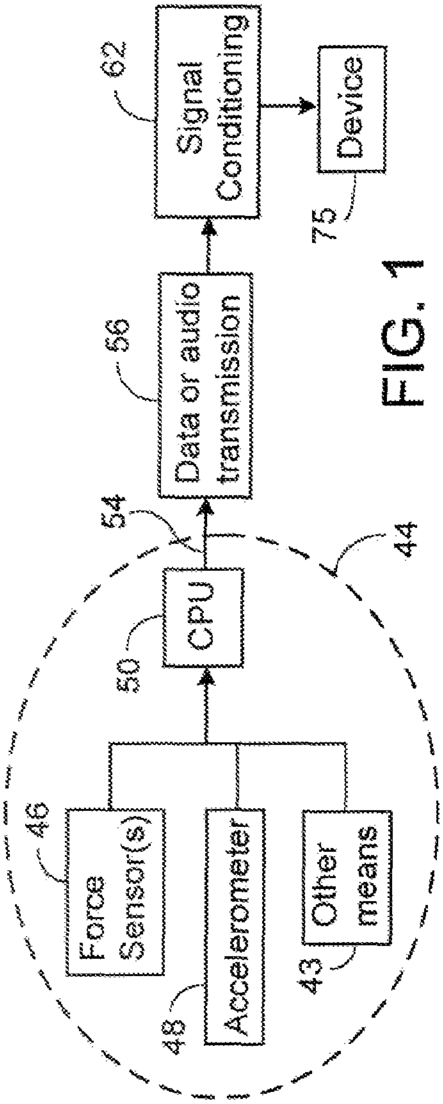
FIG. 1 shows a schematic of a system that provides an optimized pleasuring experience to a second person (at a remote location) using the self-pleasuring motions of a first person as an instigating signal.
Figure 4:
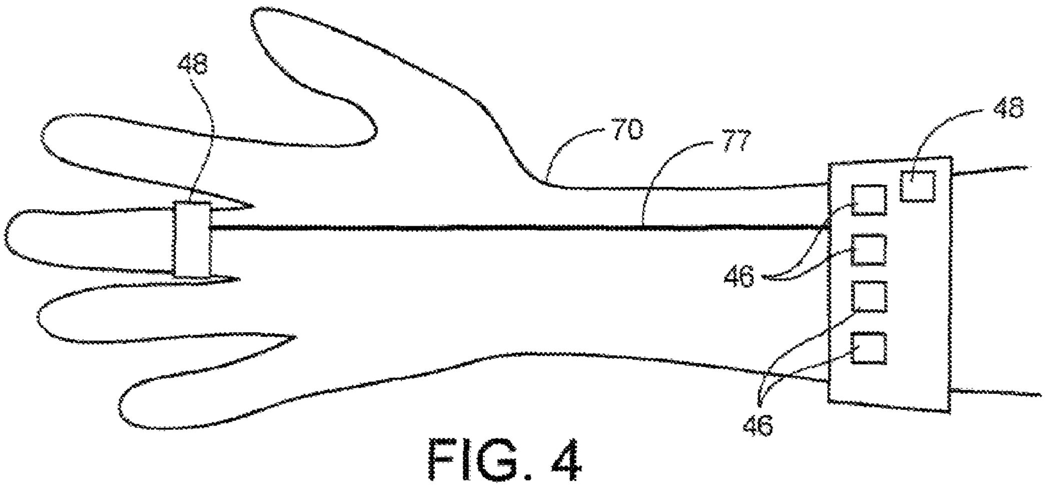
FIG. 4 shows an arm of a user with a cuff containing strain sensors and accelerometer.

FIG. 1 shows a schematic of a system that provides an optimized pleasuring experience to a second person (e.g., at a remote location) using the self-pleasuring motions of a first person as an instigating signal. The motions of the first person at a first location are measured by at least one input device 44 which includes sensors such as strain, pressure or galvanic sensors 46 to measure contraction of muscles in the forearm of the first person. For massage applications the sensors may also be mounted in an input mannequin. Accelerometer 48 provides additional information to a first central processing unit 50. First central processing unit 50 (and potentially a set of associated front-end electronics) converts the raw sensor data into a digital signal that may be reduced to a time-sequence of hand motions of the first person that fall into specified classes and magnitudes of motion, reflecting criteria such as, amplitude, force, frequency, and direction of motion. Other means 43, such as a video camera, sensors that measure location with electromagnetic fields, a device such as shown in FIG. 4, and/or speech recognition technology may be for the sensor of input device 44. The classes (and/or magnitudes) of motion are then reduced to a series information packets 54 and transmitted via data or audio transmission means 56 to a remote location where an output correlation unit 58 is located. This transmission is performed using means know in the art, e.g., through data lines or superimposed over an audio signal of a telephone call. The object is to transmit the collected motion data from the first person to the output correlation unit.

Figure 2:
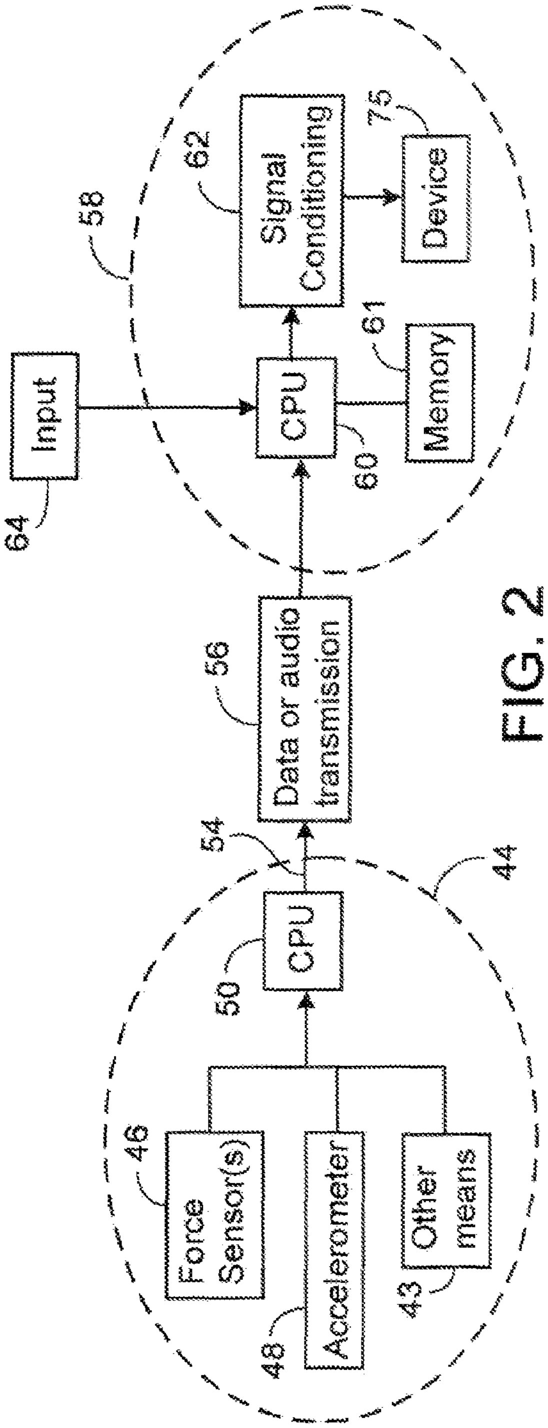
FIG. 2 shows a schematic of an embodiment of the system of FIG. 1 including an input module and additional electronics for receiving and storing control parameters from the second person.

The output correlation unit 58 includes signal conditioning electronics 62 that drive an output device 75. Conditioning electronics 62 includes digital to analog converters and the signal-to-power amplification (as known in the art) necessary to drive device 75. The type of output (e.g., physical stimulus) is dependent on the type of device 75, but in all cases there is a strong correlation between the input and output so that the result is that the recipient (i.e., second person) receives pleasure as the direct consequence of the motions of the first person. Examples of correlations include: increased pressure, speed and/or amplitude of the hand of the first person may correlate with increased vibration, oscillation, or force that the device provides to the recipient. The control parameters that provide the correlation between the sensed motions of the first person and the output from device 75 constitute a transfer function, the implementation of which is known in the art. Some of the processing may be web-based. The output device 75 may be partially under the control of the recipient, such as a vibratory dildo, a device with rotating beads, or an artificial orifice; or recipient may have no control over output device 75 such as a massage machine, Sybian or a thrusting device, FIG. 2 shows an exemplary embodiment of the system of FIG. 1 in which the output is optimized for the recipient. According to this embodiment, the recipient receives sexual pleasure that is both customized to their preference and directed by the self-pleasuring motions of the first person. In this embodiment the information packets 54 are transmitted to an output correlation unit 58. As described, the output correlation unit 58 includes a central processing unit 60, an input module 64, signal conditioning electronics 62 and data storage 61. The specific locations within the system utilized to perform the functions described, such as where the signal processing is done are immaterial to overall performance. Small modifications (such as making conditioning unit 58 integral to the device 75, or making components such as memory storage 61 and CPU 60 web-based, etc.) fall within the scope of the invention.

Data storage (e.g., memory) 61 contains data pertinent to the second person such as preferred settings, either personal preference data or personal preference data as it as they correlate with a specific partner (e.g., the first person): the basis for a customized transfer function. The purpose is to allow sexual partners not only to have an interactive sexual experience while distant, but also to optimize the experience for the receptive partner in manners that would not be otherwise possible. It improves satisfaction of partners with different physical preferences. For example, during climax one partner may prefer decreased (or no) motion while the other partner desires increased, intermittent motion, or motions of a different character than earlier in the process. Or, one person may enjoy the same type of motion for extended periods throughout the process, while the other partner prefers variation throughout the process. By having knowledge of the preferences of each receptive partner, the system may create a customized correlation between the input provided from a first person and the output provided to the receptive partner, as summarized in FIG. 4. This embodiment also includes additional input 64 from that of FIG. 1. Input 64 is provided by the recipient as described in greater detail below with respect to FIG. 3.

Output correlation with 58 functions slightly differently depend on which devices are involved. In general, a second central processing unit 60 determines the appropriate output to drive device 75 based on the measured data from the first person and deposits the data in storage 61.

Input 64 can be used by the second partner to effect the operation of device 75 directly. This input is likewise used to modify the stored transfer function. Output from the second central processing unit (i.e., CPU 60) passes through signal conditioning electronics 62 to drive device 75 thereby providing the second person a physical stimulus (e.g., a sexual stimulus) that is a function of the motions of the first person as well as their own personal preferences. Stimulation device 75 can be any electronic pleasure device designed to performance variations as a function of an external electrical signal such as a vibratory device, a thrusting device, a device with rotating beads, an artificial orifice, or a Sybian. It is important to note that the system may be used reciprocally, meaning that both partners may have an input device 44 which is utilized in the control loop of an output correlation unit 58.

This embodiment provides means for a couple to share a sexual experience remotely such that: neither person is focused on meeting the needs of the other thereby reducing their own pleasure; each partner enjoys an optimized experience, based on differing motions, even if their natural sexual motion patterns are different, thereby providing a sexual experience that may be more compatible than could be provided without the system; one or both partners may experience a self-pleasuring experience that not only has sensation beyond that of self-pleasure, but in ways that are integral with the motions of their partner.

Figure 3:
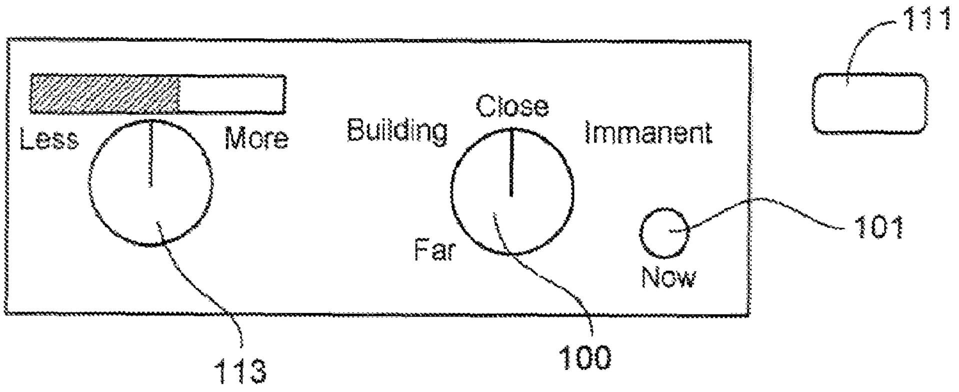
FIG. 3 shows an embodiment of a user interface, corresponding to the output correlation unit of FIG. 2, for receiving an input (e.g., control parameters) from the second person.

FIG. 3 shows one embodiment of output correlation unit 58. This device provides information to the system to compensate for timing/physiologic differences that are sometimes inherent in the preferred sexual patterns of sexual partners, as well as providing means to better correlate the climax of remotely located individuals. Physiologic data may be collected automatically with sensors 111 to measure parameters such as blood pressure, blood oximetry, skin conductivity and the like. This information can then be used by the system to automatically modify the input to the receptive partner, based on measured physiologic changes that correlate with the stages of sexual activity. Such sensing is known in the art. Physiologic sensors 111 on one or both partners (i.e., the first and/or second person) may be utilized to modulate the transfer function (and hence the output signal used to drive device 75 as a function of time, thereby to provide an optimized experience for any receptive partner. This system may, for example, be used reciprocally to enhance the experience for two or more partners simultaneously. Physiologic data may also be collected manually with a "desire" input 113, "status" input 100 and/or climax button 101. Switch 112 sets the correlation unit into learning mode, activating the manual inputs. Feedback light 102 is a query indicator, telling the recipient to provide feedback to the system. Desire input 113 allows the recipient to inform the system whether he or she desires more or less stimulus of a given type. Status input 100 allows the recipient to inform the system how far he or she is from climax. Climax input 101 allows the recipient to inform the system climax has begun. Physiologic sensors 111 and the manual input switch may be used by the system to facilitate a range of goals the partners may have, from extending or shortening the length of the overall experience for one or both partners and/or to coordinate climax of the partners. ID code data is included in the stored data in memory 61 and transmitted in packet data 54 so that the learned algorithms may be correlated with particular partners.

FIG. 4 shows an arm 70 of a first person with a cuff 72 including muscular sensors 46 and accelerometer 48. One cuff 72 may be used on each arm 70. In the preferred embodiment, cuff 72, with a plurality of sensors 46 is used to measure muscular contraction at various locations of the forearm, using force, galvanic or other methods as known in the art. These sensors may be used alone or in conjunction with at least one accelerometer 48 to provide overall motion displacement. Using such sensors the system may measure the relative motions of different fingers, direction of motion (to or from the body) as well as timing and amplitude information concerning the relative motions at different portions of the hand. One or more additional sensors and accelerometers may be located on a finger. These additional sensors/accelerometers can be held to the finger by a band, preferably, a band that does not extend to the palm-side of the hand. The band therefore holds the finger grippingly from the sides. Alternatively, adhesive can be used to attach each additional sensor and/or accelerometer directly to the users finger.

FIG. 5 shows a table with examples of transfer function correlations. Input data from sources on the left may be controlled by the transfer function to result in the output responses on the right, in any combination, with the objective being an optimized sexual experience for the recipient by modifying the actuation of device 75. Specific examples of desirable transfer function correlations have been provided elsewhere in the application. In the preferred embodiment the output (and hence the transfer function) will vary as a function of where in the process the receptive partner is at the time. Physiologic data, whether manually entered or automatically collected, provides contemporaneous information used to modify the transfer function dynamically, and thereby further optimizing the experience of the recipient. Stored control data may be used in the absence of manual input from the recipient (e.g., a remotely situated second person). The Input Data is provided by the various sources, described above, to the second central processing unit, CPU 60, where the Transfer Function (as dictated by the learned and contemporaneous physiologic data) produces an optimized output for driving device 75. The resulting physical stimulus (i.e., provided by the device 75) may be the entirety of the motion felt by the recipient, or may be superimposed upon recipient's own actions.

FIG. 6 shows a pleasure device (i.e., dildo) with pressure sensors 46*a* mounted at the tip and 46*b* at the center to measure use internal to the body and sensor 46*c* to measure the pressure applied by hand outside the body. The information collected by these sensors are transmitted to a local base unit by transmitter 80. Sensors 46, 48, and transmitter 80 are powered by power source 82. The data can then be used as the input to the transfer function to stimulate a partner. The same approach may be used on a sleeved device designed for the male organ, such as those commercially available under the trade name "Fleshlight."

While several embodiments have been described, it will be apparent to one skilled in the art how these embodiments may be varied (or combined with each other) and yet remain within the scope of the instant invention. The scope of the invention shall therefore be defined by the claims that follow.

What is claimed is:

1. A remotely operable personal massaging system, comprising:

an input device configured to receive input from a first person;

data acquisition electronics configured to receive an input signal representing the input from the input device, and configured to convert the input signal to a corresponding set of input data;

data transmission electronics in communication with the data acquisition electronics and configured to transmit an output signal representing data including a representation of the set of input data a primary pleasure device disposed at a remote location and operable to deliver a physical stimulus to a second person situated at the remote location;

an output correlation unit configured to receive the output signal from the data transmission electronics, said output correlation unit comprising signal conditioning electronics configured to drive the pleasure device according to an actuation sequence correlating to the output signal; and an input module configured to receive a set of control parameters from the second person and deliver a set of output data, corresponding to the set of control parameters, to the output correlation unit, wherein the output correlation unit is configured to adjust the actuation sequence based on the set of output data from the input module.

2. The system according to claim 1, wherein the set of control parameters corresponds to a natural sexual pattern of the second person.

3. The system according to claim 1, wherein the set of control parameters comprises physiologic data unique to the second person.

4. The system according to claim 1, wherein the input received from the input device corresponds to measured physiological motions of the first person.

5. A method of sharing sexual pleasure between remotely situated individuals, the method comprising:

measuring motions of self-pleasure of a first person using a first pleasure device;

transmitting a data signal corresponding to the measured motions to an output correlation unit;

receiving a set of control parameters from a second person;

correlating the data signal with the control parameters and creating a corresponding output signal; and driving a second pleasure device, disposed in a location remote from the first pleasure device, with the output signal, thereby to provide a physical stimulus of a sexual nature to the second person using the second pleasure device, wherein the control parameters are used to influence the physical stimulus of the pleasure device.

6. The method according to claim 5, further comprising superimposing the physical stimulus of the second pleasure device with a physiological motion of the second person.

7. The method according to claim 5, further comprising measuring motions of self-pleasure of the second person using the second pleasure device;

transmitting a second data signal corresponding to the measured motions of self-pleasure of the second person to the first pleasure device;

correlating the second data signal with a second output signal according to a second transfer function; and driving the first pleasure device with the second output signal to provide a physical stimulus of a sexual nature to the first person based on the measured motions of self-pleasure of the second person.

8. The method according to claim 5, wherein the second person has dynamic control over the control parameters of the second device, but has no direct physical control of the second device.

9. The method of claim 5, wherein correlation between the control data and the set of control parameters is executed according to a transfer function.

10. A method comprising:

receiving input from a first person;

transmitting a data signal corresponding to the input to an output correlation unit;

receiving a set of control parameters from a second person;

correlating the data signal with the control parameters and creating a corresponding output signal; and driving a pleasure device with the output signal, thereby to provide a physical stimulus of a sexual nature to the second person using the pleasure device, wherein the control parameters are used to influence the physical stimulus of the pleasure device.

11. The method of claim 10, wherein receiving input comprises measuring a physiological motion of the first person.

12. The method of claim 10, wherein receiving input comprises measuring motions of self-pleasure of the first person.

13. The method of claim 10, wherein the input comprises a frequency of vibration, an amplitude of vibration, a change in direction or magnitude of an applied force, or voice data.

14. The method of claim 10, wherein the control parameters comprise data specific to the second person.

15. The method of claim 10, wherein the control parameters comprise measured data associated with blood pressure, blood oximetry, or skin conductivity of the second person.

16. The method of claim 10, further comprising storing the set of control parameters.

17. The method of claim 10, wherein the control parameters comprise an amplitude modification imposed manually by the second person, a frequency modification imposed manually by the second person, a force modification imposed manually by the second person, a force modification imposed manually by the second person, a direction modification imposed manually by the second person, data associated with vocalizations of the second person, or an auxiliary motion modification imposed manually by the second person.

18. The method of claim 10, wherein the control parameters comprise physiologic data sensed on the body of the second person, or data associated with an input imposed by the second person that is dissimilar from the input received from the first person.

19. The method of claim 10, further comprising varying the output signal as a function of time.

20. The method of claim 10, wherein correlation between the control data and the set of control parameters is executed according to a transfer function.

21. A remotely operable personal massaging system, comprising:

one or more sensors configured to measure a physiological motion of a first person;

data acquisition electronics configured to receive an input signal representing the measured physiological motion from the sensors, and configured to convert the input signal to a corresponding set of motion data;

data transmission electronics in communication with the data acquisition electronics and configured to transmit an output signal representing data including a representation of the set of motion data to a remote location;

a primary pleasure device disposed at the remote location and operable to deliver a physical stimulus to a second person situated at the remote location;

an output correlation unit disposed at the remote location and configured to receive the output signal from the data transmission electronics, said output correlation unit comprising signal conditioning electronics configured to drive the pleasure device according to an actuation sequence correlating to the output signal; and an input module configured to receive a set of control parameters from the second person and deliver a set of output data, corresponding to the set of control parameters, to the output correlation unit, wherein the output correlation unit is configured to adjust the actuation sequence based on the set of output data from the input module.

22. The system according to claim 21, wherein the sensors are disposed in a secondary pleasure device operable by the first person.

* * * * *